(12) United States Patent
Vannucci et al.

(10) Patent No.: US 7,628,074 B2
(45) Date of Patent: Dec. 8, 2009

(54) SYSTEM AND METHOD FOR MOTION CAPTURE IN NATURAL ENVIRONMENTS

(75) Inventors: Giovanni Vannucci, Red Bank, NJ (US); Wojciech Matusik, Lexington, MA (US); Daniel Vlasic, Cambridge, MA (US)

(73) Assignee: Mitsubishi Electric Research Laboratories, Inc., Cambridge, MA (US)

( * ) Notice: Subject to any disclaimer, the term of this patent is extended or adjusted under 35 U.S.C. 154(b) by 380 days.

(21) Appl. No.: 11/686,507

(22) Filed: Mar. 15, 2007

(65) Prior Publication Data

US 2008/0223131 A1    Sep. 18, 2008

(51) Int. Cl.
*G01H 5/00* (2006.01)
(52) U.S. Cl. .......................... 73/597; 73/865.4
(58) Field of Classification Search ............. 73/597, 73/865.4
See application file for complete search history.

(56) References Cited

U.S. PATENT DOCUMENTS

| | | | | |
|---|---|---|---|---|
| 4,371,945 | A * | 2/1983 | Karr et al. ................... | 702/160 |
| 6,002,974 | A | 12/1999 | Schiffmann | |
| 7,451,056 | B2 * | 11/2008 | Flentov et al. .............. | 702/141 |
| 2005/0256689 | A1 * | 11/2005 | Schulz ........................ | 703/11 |
| 2007/0208542 | A1 * | 9/2007 | Vock et al. .................. | 702/187 |

FOREIGN PATENT DOCUMENTS

JP    2005181088 A  *  7/2005

OTHER PUBLICATIONS

Bruderlin et al., "Motion signal processing," Proceedings of SIGGRAPH 95, pp. 97-104, 1995.
Witkin et al, "Motion warping," Proceedings of SIGGRAPH 95, pp. 105-108, 1995.
Gleicher, "Retargetting motion to new characters," Proceedings of SIGGRAPH 9, pp. 33-42, 1998.
Kovar et al., "Motion graphs," ACM Transactions on Graphics 21, 3, pp. 473-482, 2002.
Arikan et al., "Motion synthesis from annotations," pp. 402-408, 2003.
Hightower et al., "Location systems for ubiquitous computing," IEEE Computer 34, 8, pp. 57-66, 2001.

(Continued)

*Primary Examiner*—Hezron Williams
*Assistant Examiner*—Nashmiya S Fayyaz
(74) *Attorney, Agent, or Firm*—Dirk Brinkman; Gene Vinokur (57) ABSTRACT

A system captures motion data in natural environments. A set of sources and a set of sensors are arranged on an object such as a human body. Each source emits ultrasonic signals detected by the sensors. A driver module is also arranged on the body. The driver module generates the ultrasonic signals for the set of sources and timing signals for the set of sensors. Distances between the set of sources and the set of sensors are measured based on a time of flight of the ultrasonic signals. Three dimensional locations of the set of sources and the set of sensors are determined from the distances. The distance measurements are refined using inertial components that provide rotation rates and accelerations. All these measurements together yield poses or configurations of the object.

15 Claims, 6 Drawing Sheets

OTHER PUBLICATIONS

Welch et al., Motion tracking: No silver bullet, but a respectable arsenal, IEEE Computer Graphics and Applications, special issue on Tracking 22, 6, pp. 24-38, 2002.

Foxlin et al., "Constellation: A wide-range wireless motion-tracking system for augmented reality and virtual set application," Proceedings of SIGGRAPH 98, pp. 371-378, 1998.

Ward et al., "A new location technique for the active office," IEEE Personal Communications 4, 5, pp. 42-47, 1997.

Priyantha et al., "The cricket location-support system," Proceedings of the 6th Annual ACM International Conference on Mobile Computing and Networking (MobiCom '00), 2000.

Randell et al., "Low cost indoor positioning system," Ubicomp 2001: Ubiquitous Computing, pp. 42-48, 2001.

Foxlin et al., Weartrack: A selfreferenced head and hand tracker for wearable computers and portable VR, ISWC, pp. 155-162, 2000.

* cited by examiner

SYSTEM AND METHOD FOR MOTION CAPTURE IN NATURAL ENVIRONMENTS

FIELD OF THE INVENTION

This invention is related generally to motion capture, and more particularly to capturing motion of objects in natural environments using sensor placed on the objects.

BACKGROUND OF THE INVENTION

Motion capture is used extensively in computer animation, Bruderlin et al., "Motion signal processing," Proceedings of SIGGRAPH 95, pp. 97-104, 1995, Witkin et al, "Motion warping," Proceedings of SIGGRAPH 95, pp. 105-108, 1995, Gleicher, "Retargetting motion to new characters," Proceedings of SIGGRAPH 9, pp. 33-42, 1998, Kovar et al., "Motion graphs," ACM Transactions on Graphics 21, 3, pp. 473-482, 2002, and Arikan et al., "Motion synthesis from annotations," pp. 402-408, 2003.

Motion capture transfers expressive performances of real actors to fantastic and realistically appearing characters. An entire industry has emerged in support of these activities and numerous recordings of human performances are now available in large motion repositories.

However, conventional motion capture requires collection in a pristine studio setting. That inhibits the broader use of motion capture in natural environments. As a result, motions such as running, skiing, and driving are simply never acquired, while others such as golf swings and football games are recorded in unnatural environments, which may affect the recorded performances.

Extended hour-long theatrical performances, which could be captured by current motion capture systems, are rarely seen or recorded, because doing so requires large audience-free studios and an excessive cost. Recording everyday human motions in natural environments is not possible.

The lack of comprehensive motion data and the exclusiveness of current motion-capture systems impair advanced computer graphics, and prevent broader application of motion processing in design of intuitive user interfaces, monitoring of medical rehabilitation, and many other applications.

The success of data-driven methods is conditioned on practical availability of large and varied data sets. An inexpensive and versatile motion-capture system could contribute to the collection of large data sets orders of magnitude larger than the current motion repositories. This enhanced infrastructure could then support large-scale analysis of human motion including its style, efficiency, and adaptability.

Several motion capture systems have been described. The advantages and disadvantages are presented in several surveys, Meyer et al., "A survey of position-trackers," Presence 1, 2, pp. 173-200, 1992, Hightower et al., "Location systems for ubiquitous computing," IEEE Computer 34, 8, pp. 57-66, 2001, and Welch et al., "Motion tracking: No silver bullet, but a respectable arsenal, IEEE Computer Graphics and Applications, special issue on Tracking 22, 6, pp. 24-38, 2002.

Optical, electromagnetic, electromechanic, inertial, and acoustic systems are now evaluated for motion capture in natural environments.

Optical motion capture places retro-reflective markers or light emitting diodes on a body. Three-dimensional marker locations are determined using triangulation methods from the images recorded with cameras. Those systems are favored for computer animation and the film industry because of their accuracy and fast update rates. The disadvantages of that approach are cost and lack of portability.

Electromagnetic systems detect the location and orientation (pose) of each marker using the magnetic field generated by a large coil. Those systems offer good accuracy and medium update speeds. Although more portable than optical motion capture, electromagnetic systems are heavy, expensive, and consume a lot of power.

Electromechanic systems require an actor to wear an exoskeleton. In those systems, joint angles are measured directly, e.g., using electric resistance. Direct estimates of location cannot be acquired. The exoskeleton is uncomfortable and difficult to wear for extended time periods.

Inertial motion capture systems measure rotation of joint, angles using gyroscopes or accelerometers placed on each body limb. Like electromechanical systems, they cannot measure location and distances directly for applications that must sample the geometry of objects in the environment. More importantly, the measurements drift by a significant amount over extended time periods.

An acousto-inertial system for indoor tracking applications is described by Foxlin et al., "Constellation: A wide-range wireless motion-tracking system for augmented reality and virtual set application;" Proceedings of SIGGRAPH 98, pp. 371-378, 1998. That system requires a constellation of transponder beacons mounted at known, locations of a ceiling. Obviously, that system is not mobile, and cannot be used outdoors.

In the Bat system, an ultrasonic emitter is worn by a user and receivers are placed at fixed locations in the environment. Ward et al., "A new location technique for the active office," IEEE Personal Communications 4, 5, pp. 42-47, 1997. The emitter sends an ultrasonic pulse when triggered by an RF signal from a central system.

The Cricket location system employs a number of ultrasonic beacons placed in the environment, Priyantha et al., "The cricket location-support system," Proceedings of the 6th Annual ACM International Conference on Mobile Computing and Networking (MobiCom '00), 2000. The beacons send ultrasonic pulses along with RF signals at random times in order to minimize possible signal interference. That allows multiple receivers to be localized independently. A similar system is described by Randell et al., "Low cost indoor positioning system," Ubicomp 2001: Ubiquitous Computing, pp. 42-48, 2001. The main difference in the latter system is that the beacons are connected to a central controller that sends RF synchronization signals to the receivers and orders the beacons to send pulses in succession.

The WearTrack system augments reality applications using a single ultrasonic beacon placed on one of the user's finger and three detectors arranged in a fixed relationship to each other on a head set. The system also requires an inertial head orientation module that uses piezoelectric gyroscopes, and solid-state accelerometers and magnetometers. The system needs to be triggered by a unique IR code from the headset, Foxlin et al., "Weartrack: A selfreferenced head and hand tracker for wearable computers and portable VR, ISWC, pp. 155-162, 2000.

SUMMARY OF THE INVENTION

The invention provides a wearable, low-cost, low-power motion capture system that can acquire motions in natural environments for extended periods of time. Ultrasonic time-of-flight measurements, linear accelerations, and angular velocities are acquired by a set of miniature sensors distributed over a wearable garment. This information is then used to reconstruct joint configurations of a human body.

The system uses an array of small, low-cost, low-power ultrasonic sources and sensors placed on the body of a person. The sources sequentially emit ultrasonic pulses, which are detected by the sensors and processed to yield distance measurements for all source-detector pairs. To increase the sampling rate and alleviate visibility problems, each sensor is also co-located with a three-axis accelerometer and a one- and two-axis gyroscope. This is equivalent to a single three-axis gyroscope, for measuring linear accelerations and angular velocities respectively. Data from all the different sensors are processed by an extended Kalman filter (EKF) to determine joint configurations for the body.

The system is completely wearable and autonomous, and does not require any external devices or signal sources for data collection.

DETAILED DESCRIPTION OF THE PREFERRED EMBODIMENTS

Motion Capture from Distances

Figure 1A:
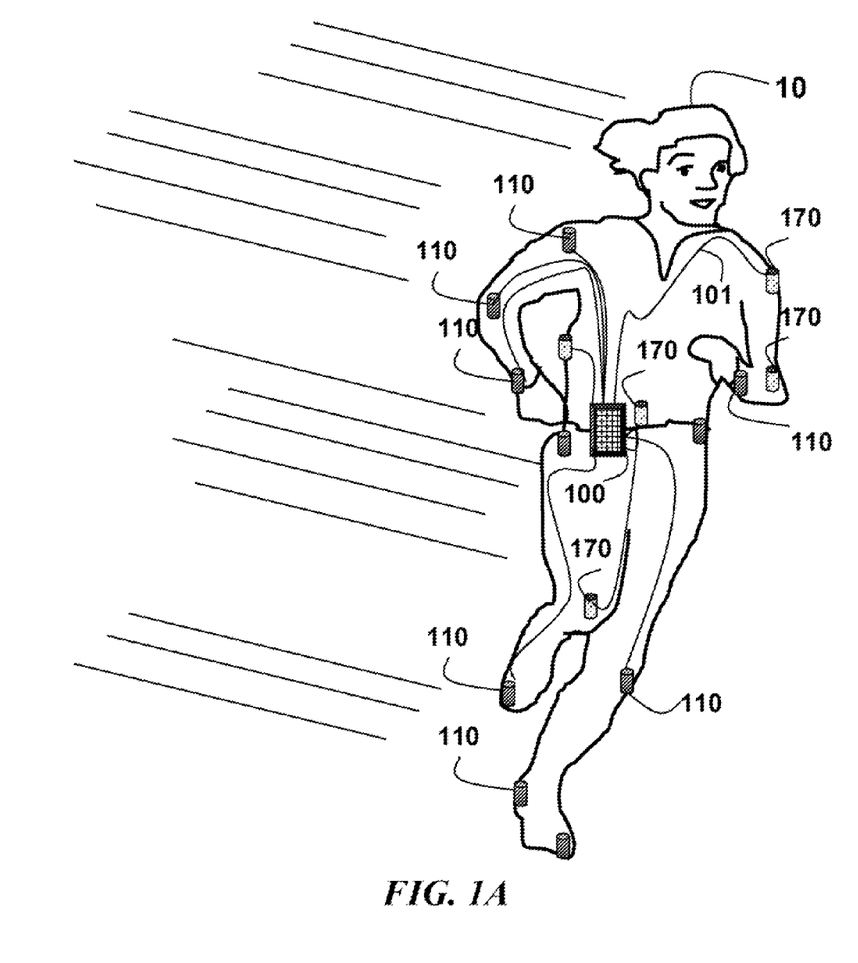
FIG. 1A is schematic of a motion capture system according to an embodiment of the invention worn by a user.

As shown in FIG. 1A, the embodiments of our invention provide a system and method for capturing motion of an object, e.g., a person 10. That is, in the preferred embodiment the object is articulated, which means the object includes rigid members, e.g., head, limbs and torso, connected at joints, e.g., elbows, ankles, knees, neck, etc.

However, it should be understood that the invention can also be used with deformable objects, i.e., objects that can change in shape and volume, or objects that are both articulated and deformable. For example, the object can be animate, i.e., a living thing such as a tree moving in the wind, or an animal, or the object can be inanimate.

The motion of the person, at any time instant, can be determined from distance measurements between different locations on the body of the person.

A set of ultrasonic signal sources 170 and signal sensors 110 are arranged on a user 10. A particular source and sensor form a pair. The sources and sensors can all move with respect to each other. The system continuously measures pairwise distances between the sources and the sensors. Then, based on a matrix of pairwise distances between the sources and sensors, it is possible to determine the 3D locations of all the sources and sensors, with respect to a global coordinate system.

The sensors can also be co-located with inertial components, i.e., three-axis accelerometers and three-axis gyroscopes. This enables the system also to measure orientation and translation of the sensors.

Given the 3D locations and orientations, it is possible to determine joint angles according to an articulated skeleton model using inverse kinematics processes. A more interesting method is to determine the joint angles directly from an incomplete distance matrix. We extend inverse kinematics methods to work with distances instead of 3D locations.

System

A primary design goal is that the system must be small size and light weight, i.e., the system must be "wearable" without excessive discomfort. The battery life of the system should be several hours. The system should also have a low-cost architecture and be scalable.

The distances between the sources and the sensors can be estimated by measuring the time it takes for a signal to travel through the air from each source to each sensor. Such measurements are known as time-of-flight (TOF) measurements. TOF measurements can be done using different signal types: e.g., radio signals, light, sound, and UWB pulses. We prefer acoustic, and in particular ultrasonic, signals. Acoustic sources and sensors provide precision, low cost, and small size, and low power consumption.

Figure 1B:
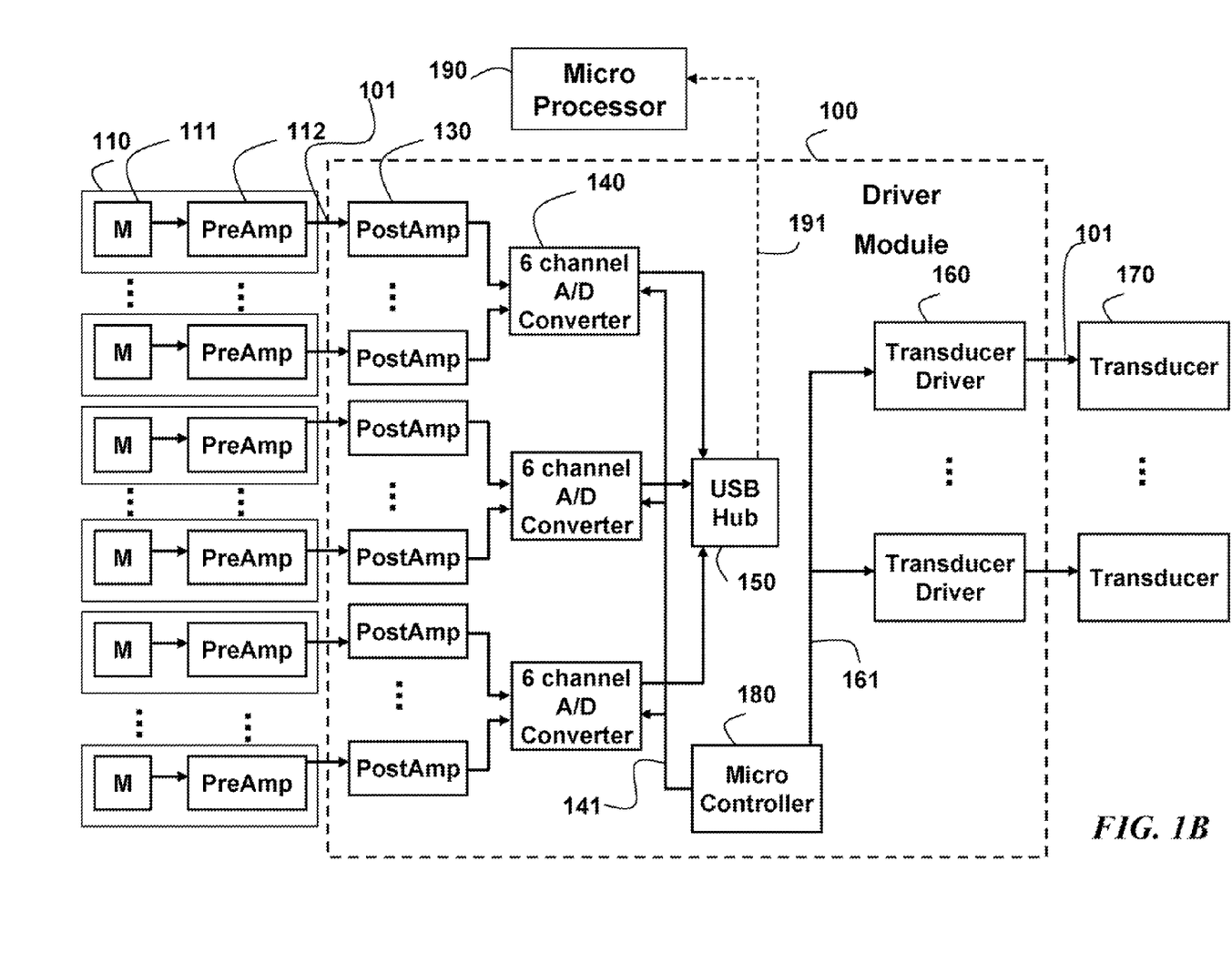
FIG. 1B is a block diagram of a motion capture system according to an embodiment of the invention.

FIG. 1B shows a structure of a portable motion capture system according to an embodiment of the invention. The system includes a driver module 100 connected to the signal sources 170 and the signal sensors 110. The sensors include a microphone 111 and a pre-amplifier 112. The sources and sensors are placed on a body of a person or on a garment worn by the person; for example, near skeleton joints. The driver module 100 communicates with a microprocessor 190, via, e.g., a USB link. Alternatively, the link is wireless. The microprocessor can be a small mobile computer, such as a laptop or smaller. The microprocessor processes motion data 191 captured by the system as described below.

The driver module 100 is housed in a plastic enclosure approximately 20 cm×20 cm×6 cm in size also arranged on the body, see FIG. 1A. The driver module is connected to the sources and sensors by cables 101. In one embodiment, we use eight sources and eighteen sensors, all free to move with respect to each other.

Thus, the entire motion capture system is mobile and can be operated in any environment, for example, in a car while driving, or while running. In contrast with the prior art, sources and sensors can all move with respect to each other. That is, the distance between any pair of source and sensor can change.

Signal Source and Sensors

We use ultrasonic signal sources, e.g., piezoelectric transducers optimized for 40 kHz. The transducers 170 are mounted on small plastic plates that are attached to the body or garment and are connected to the driver module via cables 101 that end in a standard jack. The jack is mated to a receptacle in the driver module. This has the advantages of low cost, modularity and ease of assembly.

Our ultrasonic sensors use conventional audio microphones (M) 111. This is in contrast to the usual practice in ultrasonic ranging, where the sensor is typically a piezoelectric transducer identical to the source transducer, except for its resonant detection frequency, which is optimized for maximum sensitivity at the emission frequency of the source.

We use microphones because they are small in size; e.g., cylindrical with about a 2.5 mm in diameter and 2.5 mm length, which is considerably smaller than typical piezoelectric transducers at 40 kHz. In addition, microphones have a wide angle response. Essentially, the microphone is omnidirectional, thus eliminating the need for accurate alignment with the source. This is advantageous in applications where the relative orientation of acoustic sources and sensors is, more or less, random. Furthermore, the microphones have a wide bandwidth. Therefore, the need for matching sensor resonant frequency to the sources is eliminated.

Our main concern in selecting a conventional audio-frequency microphone is that the 40-kHz frequency of our system is a full octave higher than the high end of the audible range (20 Hz-20 kHz). Although a microphone has a reduced sensitivity at 40 kHz, the microphones still provide a sufficiently strong signal, in the environments where our motion capture system is intended to operate, acoustic background noise is a dominant impairment. Even with reduced microphone sensitivity, the electrical noise introduced by the microphone pre-amplifier 112 is considerably less than the acoustic environmental noise. Under these conditions, the reduced microphone sensitivity does not cause any performance impairments.

Because we do not use coaxial jacks, we run the risk of picking up substantial amounts of electrical noise. We solve this problem by incorporating the 40-dB pre-amplifier 112 in the sensor 110. The use of small-size surface-mount components results in a small sensor 110, e.g., 1 cm×2 cm that can be mounted on a garment like a conventional button through mounting holes sized to be compatible with standard button-attachment tools.

Driver Module

The driver module 100 includes post-amplifiers 130 connected to A/D converters 140, which in turn are connected to a USB hub 140. Transducer drivers 160 are connected to the transducers 170. A micro controller 180 provides timing signals to the A/D converters 140 and ultrasonic signals 161 for the transducer drivers 160.

The post-amplifiers 130 further amplify the analog signals before the signals are digitized by the A/D converters 140.

Inertial Components

Figure 1C:
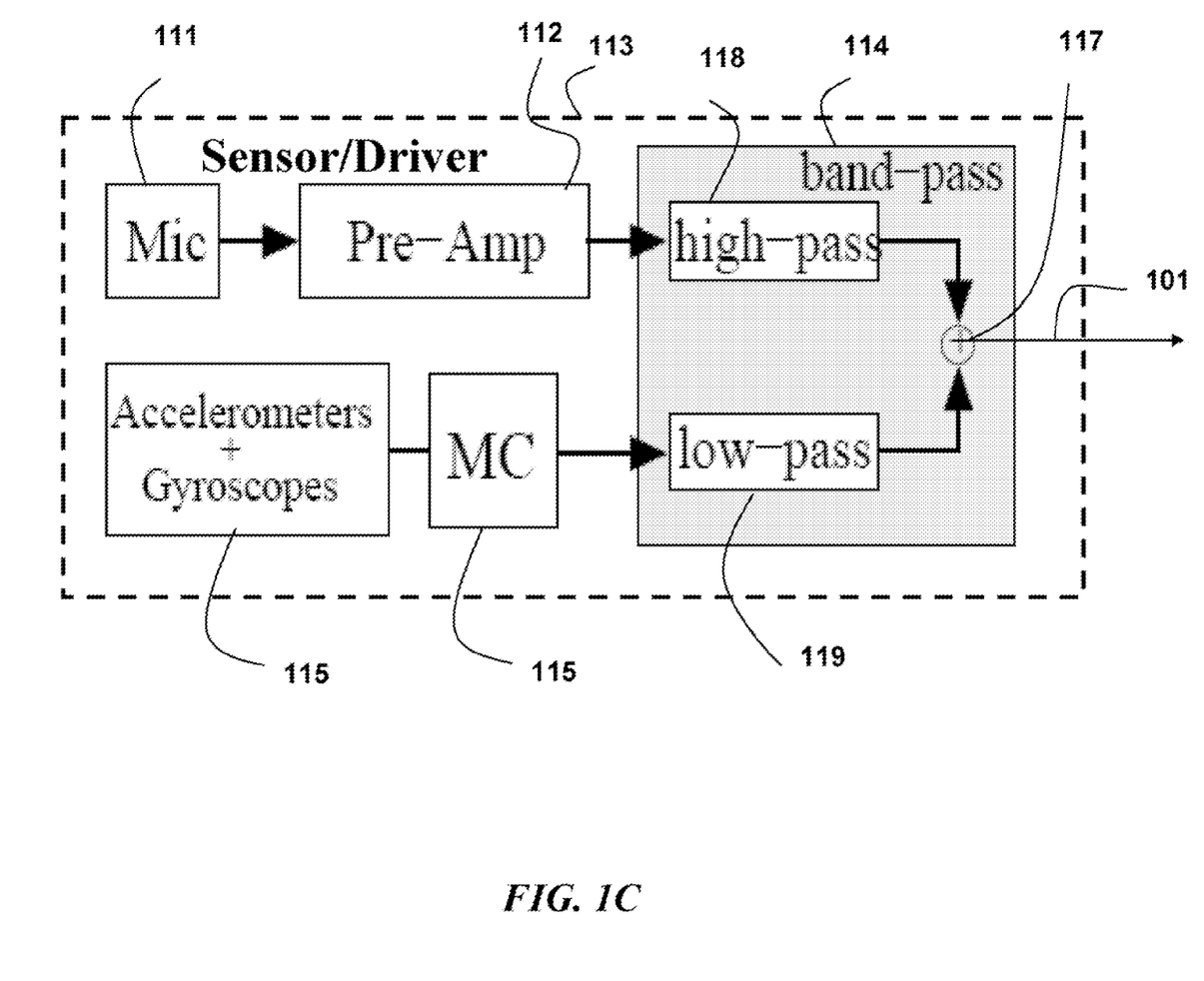
FIG. 1C is a block diagram of a signal detector and driver according to an alternative embodiment of the invention.

For an alternative embodiment. FIG. 1C shows a combined sensor/driver 113, which includes the microphone 111, pre-amplifier 112 and multiplexing filters 114. The sensor/driver also includes an inertial sensor 115, e.g., the three-axis accelerometer and the three-axis gyroscope, connected to a microcontroller 115. The microphone signal is high-pass filtered 118, while the signal from the inertial components are low-pass filtered 119.

We use the three-axis accelerometer, and the three-axis gyroscope to measure the six degrees of motion freedom of locations on the body. The microcontroller 115 includes on-chip analog-to-digital, converters that are used to sample the accelerometer and gyroscope signals at the rate of about 140 Hz. The sampled data are encoded into a single digital signal at a bit rate of about 13 kHz, including error-protection to insure accurate measurements. The encoding is described in greater detail below The digital signal is multiplexed 117 together with the analog ultrasonic signal but using a different frequency range, so that both signals can be conveyed using a single wire 101. The ultrasonic signal occupies the frequency range of 40±2.5 kHz. The low bit rate of the inertial signals allows frequency multiplexing without mutual interference as the two signals are passed through corresponding high- and low-pass filters 118-119, and superimposed on the single wire 101 without significant mutual interference.

Figure 1D:
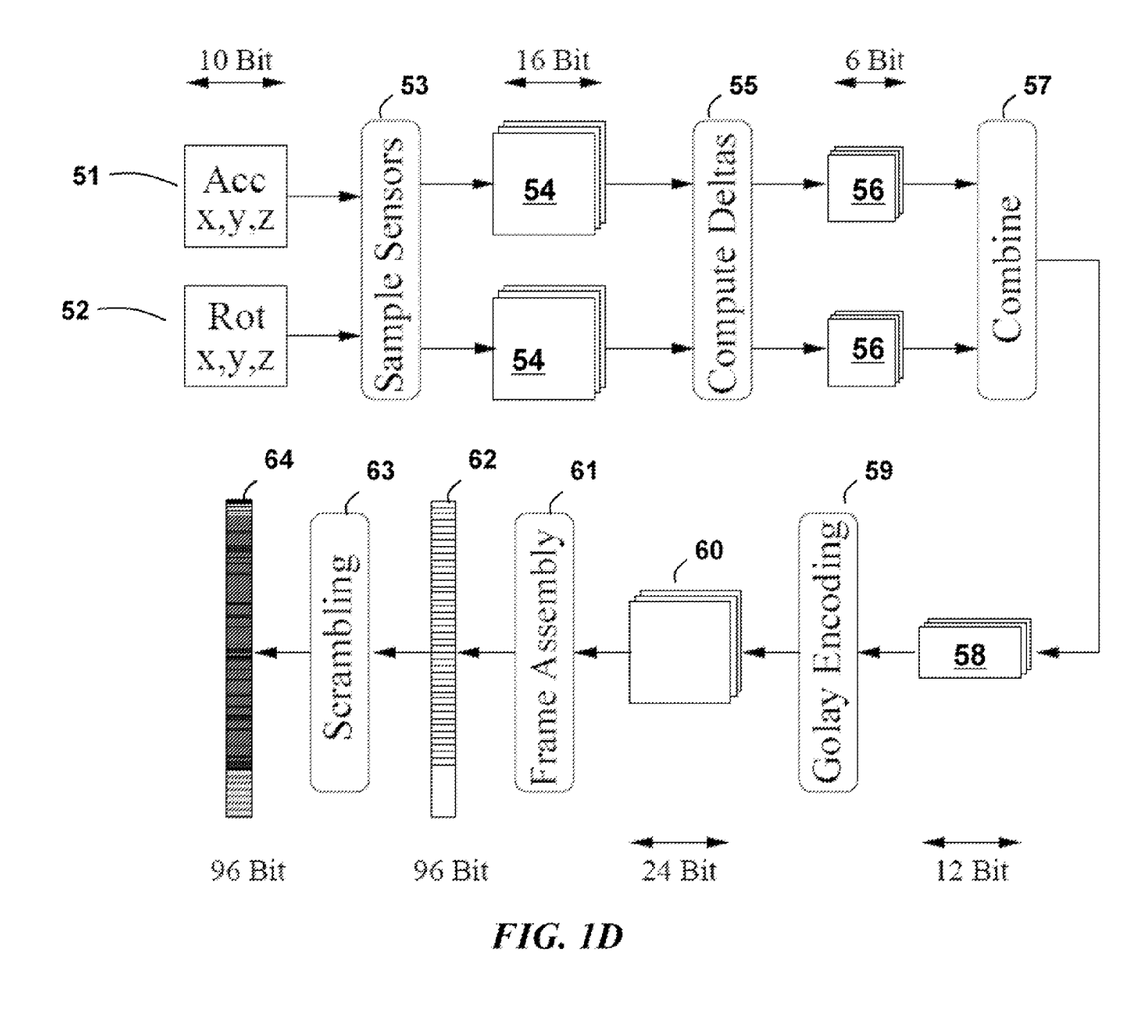
FIG. 1D is a block diagram of a signal encoder according to an embodiment of the invention.

To keep the digital data at a high frame rate, while robust to errors and transfer noise, we encode and scramble the signal using the microprocessor as shown in FIG. 1D. The 10-bit values 51-52 for the linear acceleration $(a_x, a_y, a_z)$ and angular velocity $(g_x, g_y, g_z)$ are sampled 53 sixty-four times for each data point, and accumulated to yield higher resolution 16-bit values 54, and deltas (differences) are determined 55, making maximal use of the 16-bit register of the microprocessor, The data values that are actually sent are 6-bit round-offs 56 of these 16-bit values. However, delta modulation 55 is used to avoid error propagation. Internal to the microcontroller, we keep track of the rounding error.

The quantized 6-bit values 56 are combined 57 to form three 12-bit words 58, Each 12-bit word is encoded 59 with error-correction extended Golay (24,12)-code "expanding" the values to three 24-bit code words 60, able to correct pattern errors of up to 3 bits.

The three 24-bit code words are interleaved 61 to build a 96-bit frame 62 including five 15-bit chunks, prefaced with a 15 bit frame marker entity (set to zero at this point) that indicates the beginning of each frame. The three spare bits in every frame (3×24=72 vs. 75=5×15 of available bits) can be used for auxiliary data, such as temperature measurements that are available from our microcontroller.

The assembled data, frame is scrambled 63, i.e., we XOR the frame with a pseudo-random sequence of length 16×75. This turns each frame marker, which is initially set to all zeros, into one of the 16 unique repeating values, enabling the data receiver to lock on the beginning of each frame when processing our data. A full set of 16 frames, each of which has a different frame marker, is called a super-frame. The main reason for scrambling the frame with a random bit-pattern is that this step turns the repeating structure of the frames (depending on the sensor measurements) into a more random, bit pattern that improves the stability of the signal.

At this point, a bit is added into each one of the six chunks, thus making them each 16 bits long, for the purpose of DC compensation. These DC-compensation bits are set so as to keep the balance between zeros and ones as close as possible to 50-50, thus enabling AC coupling for signal transmission of the 96-bit frames 64.

A/D Converers

In one embodiment, we use three 6-channel A/D converters with USB connections. Each converter samples each channel at about 140,000 samples per second.

Because the frequency of the transducers 170 is about 40 kHz with a bandwidth of about 5 kHz, a minimum Nyquist sampling rate required for accurate representation of the waveforms is 85 kHz. Our 140-kHz sampling rate provides a substantial over-sampling margin for easy reconstruction of the sampled signals. In our system, the signals are sampled with a resolution of 16 hits so that the 140 kHz sampling rate for eighteen sensors results in an overall data rate of about 5 Mbytes/s (i.e., 2 bytes/sample×18 channels×140 k samples/s).

This is well within the throughput capabilities of the USB interface, so that the sampled signals can be conveyed to the processor 190 in real time and immediately stored. The choice of a 16-bit resolution provides our system with a dynamic range of over 90 dB. This wide dynamic range means that no automatic gain control or calibration is needed. Because the distance between sources and the sensors varies from as little as a fraction of a centimeter to as much as about a meter, as the body is in motion, the wide dynamic range insures that the sampled signal is accurate regardless of distance. The data samples can also be compressed before storing.

The microcontroller 180 has two tasks. First, it generates the timing (clock) signals 141 to synchronize all the converters 140. Second, the microcontroller generates the signals 161 for the ultrasonic transducers 170. Because the signals applied to the transducers 170 must be stronger than the signal that can be generated by the microcontroller, we use the transducer drivers 160 to amplify the signals.

Hardware Operation

In a conventional ultrasonic ranging system, there is a single ultrasonic source and a single sensor. At regular intervals, the source emits a short burst of ultrasonic energy, i.e., a pulse. For example, the pulse might be ten cycles at 40 kHz. The observed time delay, i.e., time of flight, between emission of the pulse and sensing by the sensor is proportional to the distance between the two.

Because the signals propagates through the air and bounces off objects in the environment, the sensor detects several pulses at different times. The earliest detected pulse is the one corresponding to a line-of-sight (LOS) propagation that is used to determine the distance. Generally, subsequently detected pulses are progressively weaker as later arriving pulses travel further through the air.

After a pulse is emitted, the system must wait long enough, before emitting the next pulse, for the reflected pulses to become so weak that they are not mistaken for the LOS detection of the next pulse. In our system, we need to distinguish pulses emitted by different sources.

To accomplish that, the sources emit, pulses at different times, in a predetermined sequence, which is then repeated. That is the ultrasonic signals are time multiplexed pulses. The time separation between pulses from different sources is long enough to insure that reflected pulses from one source are not confused with the LOS pulse from a next source in the sequence. In our system, we have selected a time interval of about 8 ms between pulses from different sources. At the speed of sound at normal temperatures, this corresponds to a distance of about 2.75 m that a pulse has to travel before another pulse is emitted by another source. This distance is greater than the extremities of a body fully extended, it should be noted, the inter-pulse time can be extended for larger objects.

This time interval is sufficient to insure that the LOS pulses are considerably stronger than any reflected pulses from the previous source. Because our system includes eight sources, a time interval of 8 ms means that the entire sequence of eight pulses from the eight sources takes 64 ms. Therefore, each individual source emits pulses at 64 ms intervals. Thus, an estimate of the pose (location and orientation) of the various parts of body is refreshed every 64 ms, or a rate of about 16 Hz.

The number of sources affects the refresh rate. Doubling the number of sources halves the refresh rate. Alternative methods can be used to distinguish pulses from different sources so that the number of sources can be increased without reducing the refresh rate.

Motion Measuring Component

The inertial components output values that are processed by the microcontroller 115 before they can be further processed. There is a trade-off between the sampling rate and the amount of data being sent over the wire (speed vs. size). Sampling the motion detectors at 140 Hz provides the temporal resolution that we want. The sampling-rate, the sample size and the frame size are strongly linked; changing one parameter influences the others. At 140 Hz, with the speed limitations of the microcontroller and the frequency considerations of the digital signal (no interference with the ultrasonic signal, so increasing the frequency was not a preferable solution) sending 6-bit values is our choice.

Using an error-correcting code such as Golay (24,12) on the 12 bit words (2×6 bits) allows us to substantially lower the amplitude of the digital signal in the output signal of the detector boards so that the interference with the ultrasonic signal can be reduced, The Golay code corrects up to 3 bit errors in a 24-bit code word and detects up to 4 bit errors.

Bit error-triggering events from the environment usually occur in bursts. To lower the risk of suffering from more than 4 bit errors (which could not be detected and result in erroneously decoded values) in a code word, the three code words are interleaved. Doing this, a noise burst might still distort multiple bits in a row, but they will be part of three different code words each of which suffers from fewer errors than it would if no interleaving had been applied.

Data Processing

In one embodiment of the invention, the sensed data 191 are processed off-line. Data from each sensor is stored in a separate file. We use batch-processing to convert sampled acoustic signal first to distance measurements along with a confidence measure for each measurement. Next, we combine distance measurements from multiple sensors to extract 3D locations over time. Based on the tracked 3D locations, we can determine the configuration, i.e., the location and orientation, or pose, of the underlying object, e.g., the body of the user wearing the sensors.

Acoustic Signal Processing

Now we describe how to process the acoustic signal from each microphone to extract distance measurements. We note that the acoustic signal can be isolated from the complete signal by band-passing the signal around 40 kHz; thus rejecting the digital signal. We also note that the acoustic signal is perfectly synchronized with the emitted pulses. In other words, we know precisely when pulses from ultrasonic transducers are sent because the microcontroller issues both the clock signal for the A/D converters and the signal to the transducer drivers.

The sampled signal is partitioned into frames, where each frame corresponds to our setting of maximum distance traveled by the pulse—2.75 m, which corresponds to 1120 samples.

Figure 2A:
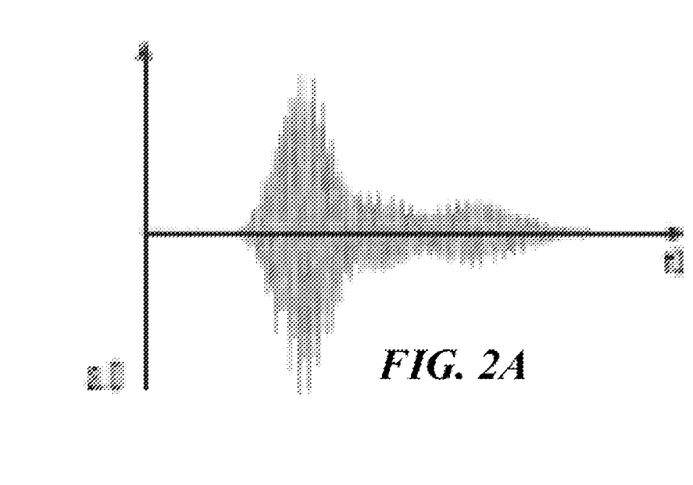
FIGS. 2A-2D are traces of acoustic signals processed according to an embodiment of the invention.
Figure 2B:
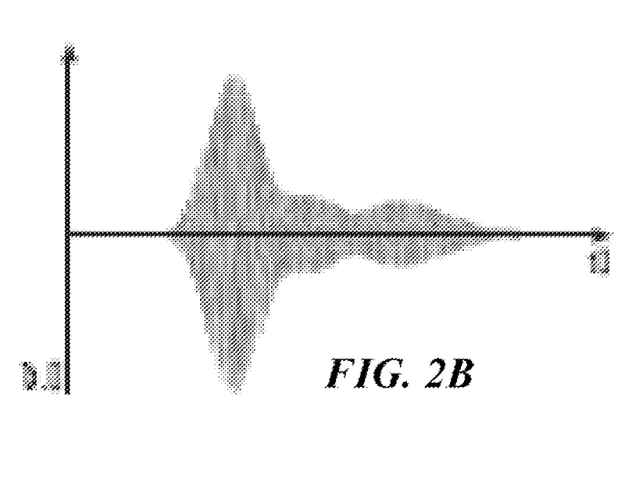

The steps to extract the distance for each frame are as follows. First, we use a band-pass filter to eliminate all signal frequencies that are outside the range of our ultrasonic transducers (e.g., the audible frequencies), see FIG. 2A. Based on the transducer specifications, we pick a filter that is centered at 40 kHz and has a width of 5 kHz. Second, we up-sample the signal eight times in order to remove any aliasing artifacts, as well as to increase the effective timing resolution see FIG. 2B.

Figure 2C:
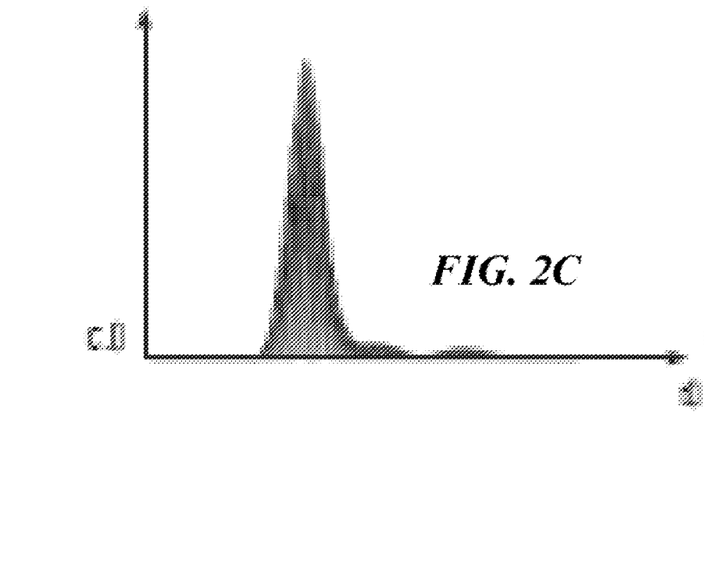

Third, we square the signal because we are more interested in the power of the signal rather than the signal itself, see FIG. 2C.

Figure 2D:
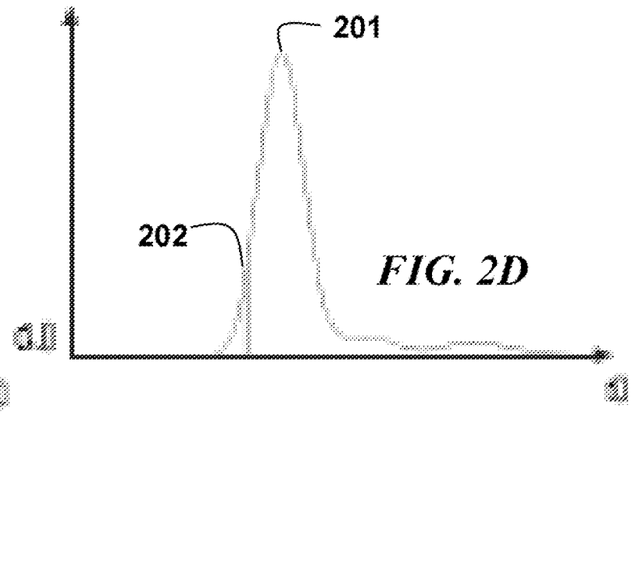

Fourth, we extract the envelope of the signal power by passing it through a low-pass filter with the cut-off frequency of 30 kHz, see FIG. 4D. We observe that tracking the location of the peak does not provide the most precise distance measurement since the gradient of the signal power envelope is low. Instead, we compute the inflection point (where the gradient is the largest), which is positioned about 40 samples after the start of the pulse. We perform a calibration for each ultrasonic transducer to compute the exact offset value in the number of samples.

The power envelope of the signal can contain multiple peaks due to reflection. Furthermore, the envelope can contain no useful peaks if there is no direct line-of-sight between the source and the detector. To deal with this problem, we associate a confidence measure w with each distance measurement, which ranges from 0 (no useful measurement) to 1 (a correct measurement). When estimating w, we take the following factors into account: signal strength (measure $w_s$), temporal continuity (measure $W_t$), and an angle between the source normal and the detector (measure $w_a$).

To incorporate the signal strength factor, we first ensure that the signal is well above (6 standard deviations) the estimated ambient noise (assumed to be a zero-mean Gaussian). We also normalize the peak values by multiplying them by their squared distance (signal strength of a spherical wave is proportional to the inverse of the squared radius), and compare them to a predetermined threshold. If the value is above the threshold then $w_s$ is set to 1. Otherwise, $w_s$ decreases with the squared inverse of the difference between the threshold and the peak value. The temporal continuity measure $w_t$ decreases below 1 when the distance measurements in neighboring frames are significantly different.

The angular confidence measure $w_a$ is computed based on the current estimates of 3D sensor locations. In our implementation, $w_a$ is set to 1, unless the angle between the source normal and the vector toward the detector is greater than 90 degrees, in which case it is 0. This tries to ensure that the detector is within the field-of-view of the source. The total confidence measure w is a product of those three measures.

Figure 3A:
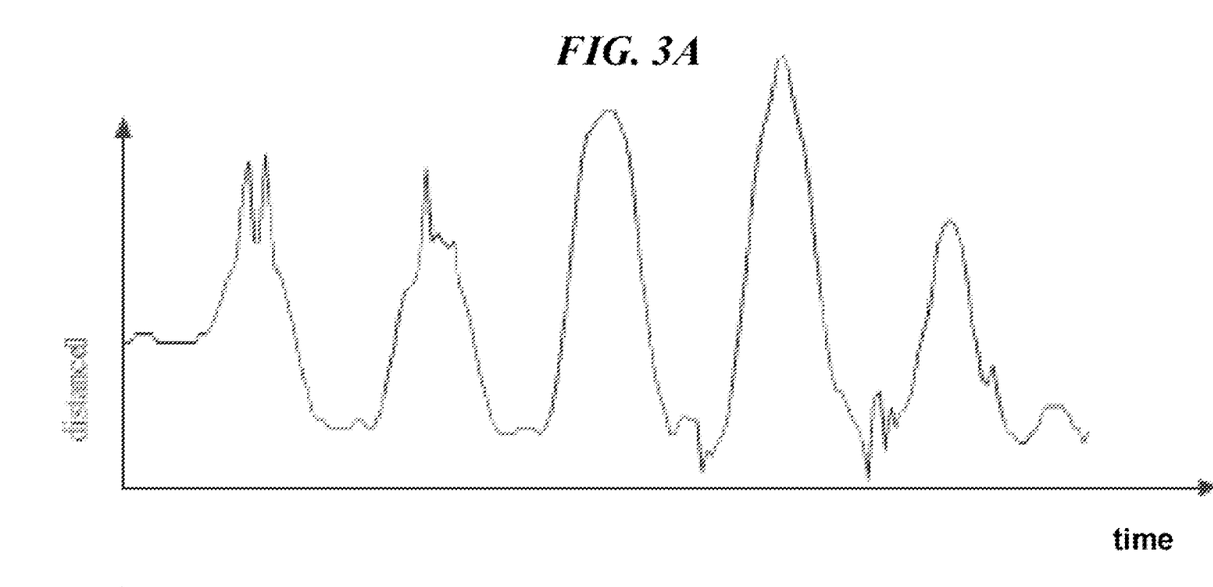
FIG. 3A is a graph of sensed distances according to an embodiment of the invention.
Figure 3B:
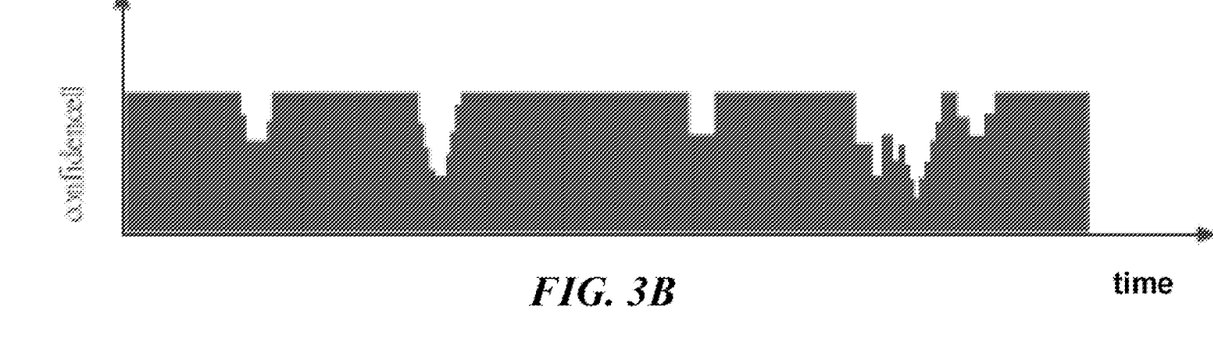
FIG. 3B is a graph of confidence measurements according to an embodiment of the invention.

FIG. 3A shows sample detected distances, and FIG. 3B the corresponding confidence measures for a source-sensor pair during a few seconds of recording. Note that low confidence corresponds to intervals where the signal reconstruction is erroneous.

We note that distance updates from each of the sources to all sensors are interleaved in time. Therefore, we upsample all our distance measurements by a factor of eight in the time domain. We obtain distances updates between the sources and sensors that are aligned in time at 128 Hz (8×16 Hz).

Inertial Signal Processing

In this section we describe the processing of the digitally encoded numbers from the inertial components, i.e., the accelerometer and the gyroscopes. The process is the reverse of the encoding shown in FIG. 1D. Similar to processing the ultrasonic data, as described above, we filter the signal before being extracting the bits. We use a low-pass filter to remove the high-frequency portions resulting from the pings.

The first step on the filtered signal is to calculate the correlation. In every super-frame, the pattern of frame markers repeats. We use this well-known repeating pattern to lock to the bit stream and find the beginning of a super-frame. When we have found its beginning in the signal, we start converting the signal levels into zeros and ones. Every "data bit" consists of multiple samples. Because of the higher sampling rate than the bit rate every bit includes approximately 10.5 samples.

Next the frames are "de-scrambled." The known patterns of the pseudo-random sequence are XOR-ed to the frames. After this step, the original frame structure is restored.

In the next step, the frames are "disassembled", that is the three Golay code-words, each of length 24 bits, are extracted. The encoded 12-bit entities (concatenated 6-bit values) are split and the resulting six values are stored for further processing. Golay encoding is helpful to correct up to thee bit errors and it allows us to detect up to 4 bit errors. Every error count exceeding this threshold is not detected and would result in erroneously decoded values.

Recovering the Object Pose

Herein, the pose is defined as including location and orientation. Furthermore, the six degree of freedom pose can be determined with respect to a global or world coordinate system. To recover the pose of a tracked subject, we use an extended Kalman filter (EKF) to combine all the measurements our system, provides; accelerations from accelerometers, angular velocities from gyroscopes, and distances from the ultra-sonic sensors.

The EKF provides a convenient and efficient framework for combining very different observations of the same system, see U.S. Pat. No. 6,002,974 issued to Schiffmann on Dec. 14, 1999 for "Vehicle rollover sensing using extended kalman filter," incorporated herein by reference.

Extended Kalman Filter (EKF)

The EKF is a non-linear function $f$ that describes the evolution of an underlying system state x, and a non-linear function h, which describes our observation of the system:

$$x_k = f(x_k-1, w_k-1), \text{ and} \quad (1)$$

$$z_k = h(xk, v_k). \quad (2)$$

where k and k−1 represent the current and the previous time step, w is the system noise encompassing information about the system that we do not know how to model, e.g., how does a human decide which torques to apply to which joints, and v is the measurement noise.

The EKF operates in two steps. First, the time is updated until it equals the time of the next observation:

$$x_k^- = f(X_{k-1}, 0) \quad (3)$$

$$P_k^- = A_k P_{k-1} A_k^T + W_k Q W_k^T \quad (4)$$

where − stands for the a priori estimate, P is the state covariance, Q is the system noise covariance, $A = \partial f / \partial x$ is the Jacobian of $f$ with respect to the system parameters, and $W = \partial f / \partial w$ is the Jacobian of $f$ with respect to the system noise parameters.

Second, the Kalman step uses the observation $z_k$ to improve on the a priori estimates of the state $x-_k$ and its covariance $P-_k$:

$$K_k = P_k^- H_k^T (H_k P_k^- H_k^T + V_k R_k V_k^T)^{-1} \quad (5)$$

$$x_k = x_k^- + K_k(Z_k - h(x_k^-, 0)) \quad (6)$$

$$P_k = (I - K_k H_k) P_k^- \quad (7)$$

where K is the Kalman gain chosen to minimize the a posteriori state covariance, R is the measurement noise covariance, $H = \partial h / \partial x$ is the Jacobian of h with, respect to the system parameters, and $V = \partial h / \partial v$ is the Jacobian of h with respect to the measurement noise parameters.

The high-level operation of the EKF is as follows. At each new observation data sample sensed, be it from an accelerometer, gyroscope, or the acoustic subsystem, advance the system time until it reaches that observation, (if necessary) using the first EKF step. Then, use the observation to get a better estimate of the state using the second EKF step. For the simplicity of implementation, ail the Jacobian matrices (A, W, H, V) for the two EKF steps are determined using an automatic differentiation code. Hence, only the functions $f$ and h are described herein.

Joint Configurations

The body structure provides constraints which can be exploited in the recovery of its joint configurations. The configuration of an articulated body is specified by the joint angles that describe configurations of shoulders, elbows, and other body joints. We use a single vector θ to assemble all joint angles in the body, and note the following forward-kinematics functions F(θ) and F(q) that compute position and orientation of body points as a function of the joint angles. The underlying EKF state in this case is:

$$x_k = \begin{bmatrix} \theta_k \\ \dot{\theta}_k \\ \ddot{\theta}_k \end{bmatrix} = \begin{bmatrix} \theta_{k-1} + \dot{\theta}_{k-1}\Delta t \\ \dot{\theta}_{k-1} + \ddot{\theta}_{k-1}\Delta t \\ \ddot{\theta}_{k-1} + w_{k-1} \end{bmatrix} = f(x_{k-1}, w_{k-1}) \quad (8)$$

where the state x contains joint angles, their velocities, and accelerations
($\theta$, $\dot{\theta}$, $\ddot{\theta}$).

The process noise w is normally distributed, and computed as the mean change in joint acceleration for a sequence of normal human motion. Accelerometer observation. An acceleration observation at frame k yields the following $$Z_k = [Z_i]_k = [\mathscr{R}\{\dot{J}_i\dot{\theta} + J_i\ddot{\theta} - g\} + v_{1i}]_k = h(X_k, V_k) \quad (9)$$

where $J = dF/d\theta$ is the positional forward-kinematics Jacobian, and $\dot{J} = dF/dt$ its time derivative, g is the upward-pointing gravity vector, $\mathscr{R}\{\cdot\}$ denotes the rotation from the global coordinate frame into the coordinate frame of accelerometer i, and $v_1$ is the accelerometer precision.

Gyroscope Observation Samples

An angular velocity observation at frame k yields the following h:

$$Z_k = [Z_i]_k = [\mathscr{R}\{J_i\dot{\theta}\} + v_{2i}]_k = h(X_k, V_k) \quad (10)$$

where $J = dF/d\theta$ is the orientational forward-kinematics Jacobian, and $v_2$ is the gyroscopic precision.

Ultrasonic Observation

A distance observation at frame k yields the following h:

$$Z_k = [Z_{ij}]_k = [\|F(\theta)_i - F(\theta)_j\| + v_{3i}]_k = h(X_k, V_k) \quad (11)$$

where $F(\theta)_i$ is the positional forward-kinematics equation for marker 1, and $v_3$ is the distance precision as determined by the ultrasonic subsystem.

Alternative Embodiments

Alternative embodiments can use signals other than ultrasonic signals for the time-of-flight measurements. For example, radio signals can be used. We can also use waveforms other than short pulses for the time-of-flight signals. For example, continuous-wave sinusoids can be used with chirping or frequency stepping to achieve the desired sampling bandwidth. An equivalent impulse response can then be derived through the use of transforms such as the Fourier transform. Alternatively, pseudo-random sequences can be used, and the impulse response can be derived through de-convolution techniques, or by computing cross correlations between transmitted and received signals, These examples are not meant to be restrictive, as many alternative waveform choices exist.

We can replace the wired connections 101 with wireless links. For example, a radio link technology such as Bluetooth can be used to interconnect the sensors 110 or the sensor/drivers 113 or the transducers 170 with the driver module 100 wirelessly. Other wireless technologies can also be used such as WiFi or infrared or others.

The various functionalities can be distributed in a different way among the various components. For example, the function of the A/D converters 140 can be incorporated into sensor/drivers 113, such that the signal sent over wired connections 101 is a multiplexed digital signal. Also, the microcontroller 115 can perform some or all of the signal processing illustrated in FIGS. 2A-2D. The microcontroller 115 can also store the signal, with or without processing, for non-real-time transfer to the driver module 100. Also, the transducers 170 can incorporate circuitry to generate the ultrasonic pulses in response to a timing signal from the driver module.

We can combine the functionality of transducers 170 with that of sensors 110 or the sensor/drivers 113. For example, the system can include a single type of remote sensor/driver/transducer that incorporates, on the same circuit board, a piezoelectric transducer for producing ultrasonic pulses, a microphone, gyroscopes and accelerometers. Such a unit can perform the functions of both transducers 170 and sensors 110 simultaneously or at different times. Also, we can just include gyroscopes and accelerometers in the transducers 170 for enhanced system accuracy.

Partial Implementations of the Embodiments

We can include only a two-axis gyroscope in sensor/drivers 113. This provides incomplete, but still useful, position and orientation information. By using a larger number of sensor, drivers 113 or transducers 170, the system can still achieve the desired accuracy in spite of the missing gyroscope axis. Depending on the availability of one- two- or three-axis gyroscope or accelerometer chips, an embodiment with a reduced number of sensed axes may be desirable.

Enhanced Implementations of the Embodiments

We can use alternative location technologies in the sensor/drivers 113. For example, we can incorporate a GPS receiver in some or all sensor/drivers 113 to provide additional positioning data and additional accuracy. In particular, it can provide absolute positioning information.

Effect of the Invention

The embodiments of the invention provide wearable motion capture system that is completely autonomous, and is capable of operating for extended periods of time in a large range of natural environments. The system acquires distance measurements between different points of the body. We determine both 3D locations of the tracked points and a pose of the skeleton pose directly from these distances.

The cost of the current system is an order of magnitude less than the cost of the cheapest conventional motion capture systems and two orders of magnitude less than a high-quality optical motion capture system. Much smaller version of the system with more sensors can be mass-produced for a few hundred dollars. This implies that this type of system can be owned and used on a daily basis by almost anyone.

The computation can be done off-line or on-line in real time. This enables the system to be used in a variety of virtual and augmented-reality applications. The system can also incorporate inertial sensors along with the acoustic sensors. The inertial sensors would provide better accuracy and faster update rates while the acoustic sensor correct for drift and ensure accurate operation of the system over extended time periods.

Although the invention has been described by way of examples of preferred embodiments, it is to be understood that various other adaptations and modifications can be made within the spirit and scope of the invention. Therefore, it is the object of the appended claims to cover all such variations and modifications as come within the true spirit and scope of the invention.

We claim:

1. A system for capturing motion data in natural environments, comprising:
a set of sources arranged on an object capable of undergoing motion, in which each source is configured to emit ultrasonic signals;
a set of sensors arranged on the object, in which each sensor is configured to detect the ultrasonic signals;

a driver module arranged on the object, in which the driver module is configured to generate the ultrasonic signals for the set of sources and timing signals for the set of sensors, and in which the ultrasonic signals are synchronized to the timing signals;

means for measuring distances between the set of sources and the set of sensors based on a time of flight of the ultrasonic signals;

a set of inertial components arranged on the object;

means for determining 3D orientations of the set of inertial components; and means for determining 3D locations of the set of sources and the set of sensors from the distances to capture motion data of the object, in which the 3D locations and the 3D orientations determine a six degree of freedom pose with respect to a world coordinate system, and wherein the six degree of freedom pose is determined using inverse kinematics processes.

2. The system of claim 1, in which the object is articulated.

3. The system of claim 1, in which the object is deformable.

4. The system of claim 1, in which the object is animate.

5. The system of claim 1, in which the object is inanimate.

6. The system of claim 1, in which a particular source and a particular sensor form a pair, which can move with respect to each other.

7. The system of claim 1, in which the 3D locations are with respect to a global coordinate system.

8. The system of claim 1, in which the set of inertial components include three-axis accelerometer, and a three-axis gyroscope.

9. The system of claim 1, in which the set of sources, the set of sensors and the set of inertial components are wearable by a user.

10. The system of claim 1, in which the set of sources, the set of sensors and the set of inertial components are connected to the means for determining the 3D locations and the means for determining the 3D orientations by a wireless link.

11. The system of claim 1, in which a frequency range of the ultrasonic signals is 40±2.5 kHz.

12. The system of claim 1, in which signals from the inertial components are low-pass filtered, and the ultrasonic signals are high-pass filtered and the low-pass and high-pass signals are carried on a signal wire before transmission to the means for determining 3D orientations of the set of inertial components.

13. The system of claim 1, in which the ultrasonic signals are time multiplexed pulses.

14. The system of claim 1, in which the pose is determined using an extended Kalman filter applied to the distances and orientations.

15. A method for capturing motion data in natural environments, comprising:

arranging a set of sources on an object capable of undergoing motion, in which each source is configured to emit ultrasonic signals;

arranging a set of sensors on the object, in which each sensor is configured to detect the ultrasonic signals;

arranging a set of inertial components arranged on the object;

determining 3D orientations of the set of inertial components;

measuring distances between the set of sources and the set of sensors based on a time of flight of the ultrasonic signals; and determining 3D locations of the set of sources and the set of sensors from the distances to capture motion data of the object, wherein the 3D locations and the 3D orientations determine a six degree of freedom pose with respect to a world coordinate system, and wherein the six degree of freedom pose is determined using inverse kinematics processes.

* * * * *